United States Patent [19]

Spinale

[11] Patent Number: 5,541,209
[45] Date of Patent: Jul. 30, 1996

[54] METHOD OF TREATING OR PREVENTING CARDIAC ARRHYTHMIA EMPLOYING AN N-SUBSTITUTED HETEROCYCLIC DERIVATIVE

[75] Inventor: Francis G. Spinale, Charleston, S.C.

[73] Assignee: Bristol-Myers Squibb Company, Princeton, N.J.

[21] Appl. No.: 293,985

[22] Filed: Aug. 22, 1994

[51] Int. Cl.$^6$ .................................................. A61K 31/41
[52] U.S. Cl. ........................................ 514/381; 514/821
[58] Field of Search ................................... 514/381, 821

[56] References Cited

U.S. PATENT DOCUMENTS 5,270,317  12/1993  Bernhart et al. ........................ 514/269

OTHER PUBLICATIONS

R. Dietz et al., "Improvement of Cardiac Function by Angiotensin Converting Enzyme Inhibition", Supplement IV Circulation, vol. 87, No. 5, May 1993, pp. 108–116.

*Primary Examiner*—Kimberly Jordan
*Attorney, Agent, or Firm*—Ellen K. Park

[57] ABSTRACT

The invention relates to the use of an N-substituted heterocyclic derivative and its pharmaceutically acceptable salts for the treatment or prevention of cardiac arrhythmia. These derivatives have the structure

I

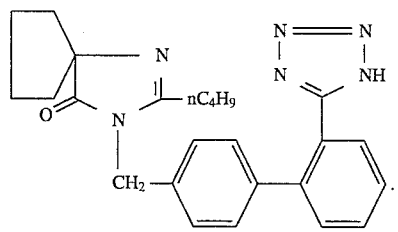

12 Claims, No Drawings

METHOD OF TREATING OR PREVENTING CARDIAC ARRHYTHMIA EMPLOYING AN N-SUBSTITUTED HETEROCYCLIC DERIVATIVE

BRIEF DESCRIPTION OF THE INVENTION

In accordance with the present invention, surprisingly and unexpectedly, it has been found that an N-substituted heterocyclic derivative having the structure

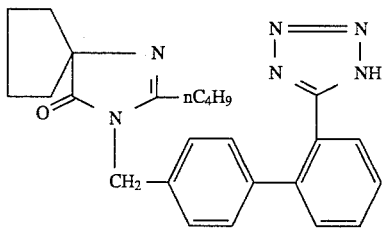

or a pharmaceutically acceptable salt thereof, may be used to treat or prevent cardiac arrhythmia. The above compound, including salts thereof and methods for making the compounds are described in U.S. Pat. No. 5,270,317 to Bernhart, incorporated by reference herein.

DETAILED DESCRIPTION OF THE INVENTION

The present invention relates to the use of a compound having the structure I or pharmaceutically acceptable salts thereof for the treatment or prevention of cardiac arrhythmia e.g., disturbance of cardiac rate or rhythm. The pharmaceutically acceptable salts of the compounds having the structure I include salts with acids such as hydrochloride, hydrobromide, sulfate, hydrogensulfate, dihydrogen-phosphate, methanesulfonate, methylsulfate, maleate, fumarate and naphthalene-2-sulfonate. The salts of the compounds having the structure I also include the salts with organic or mineral bases, for example the salts of alkali or alkaline earth metals, such as the sodium, potassium and calcium salts, the sodium and potassium salts being preferred, or with a tertiary amine such as trometamol, or else the salts of arginine, lysine or any physiologically acceptable amine.

In carrying out the method of the present invention, a compound of structure I or a pharmaceutically acceptable salt thereof, may be administered to a mammalian species in need thereof, such as dogs, cats, humans, etc., and as such may be incorporated in conventional dosage forms. Examples of conventional dosage forms of administration include forms for oral administration, such as tablets, gelatin capsules, powders, granules and solutions or suspensions to be taken orally, forms for sublingual, buccal, intratracheal or intranasal administration, forms for subcutaneous, intramuscular or intravenous administration and forms for rectal administration. For topical application, the compounds according to the invention can be used in creams, ointments or lotions.

To achieve the desired prophylactic or therapeutic effect, the dose of active principle can vary between 0.01 and 50 mg per kg of body weight per day.

Each unit dose can contain from 0.1 to 1000 mg, preferably 1 to 500 mg, of active ingredients in combination with a pharmaceutical carrier. This unit dose can be administered 1 to 5 times a day so as to administer a daily dosage of 0.5 to 5000 mg, preferably 1 to 2500 mg.

When a solid composition in the form of tablets is prepared, the main active ingredient is mixed with a pharmaceutical vehicle such as gelatin, starch, lactose, magnesium stearate, talc, gum arabic or the like. The tablets can be coated with sucrose, a cellulose derivative or other appropriate substances, or else they can be treated so as to have a prolonged or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of syrup or elixir or for administration in the form of drops can contain the active ingredient in conjunction with a sweetener, which is preferably calorie-free, methylparaben and propylparaben as antiseptics, as well as a flavoring and an appropriate color.

The water-dispersible granules or powders can contain the active ingredient mixed with dispersants or wetting agents, or suspending agents such as polyvinylpyrrolidone, as well as with sweeteners or taste correctors.

Rectal administration is effected using suppositories prepared with binders which melt at the rectal temperature, for example cacao butter or polyethylene glycols.

Parenteral administration is effected using aqueous suspensions, isotonic saline solutions or sterile and injectable solutions which contain pharmacologically compatible dispersants and/or wetting agents, for example propylene glycol or butylene glycol.

The active principle can also be formulated as microcapsules, with one or more carriers or additives if appropriate.

In addition to the products having a compound of structure I above or one of the pharmaceutically acceptable salts thereof, the compositions can contain other active principles such as, for example, other antiarrhythmic agents, tranquilizers or other drugs which can be useful in the treatment or prevention of cardiac arrhythmia or related conditions. Examples of other active principles include a beta-blocking compound, a calcium antagonist, a diuretic, a non-steroidal antiinflammatory or a tranquilizer. Therefore, the present invention includes the treatment or prevention of cardiac arrhythmia by administering a compound having the structure I or a pharmaceutically acceptable salt thereof in association with other active principles as a single pharmaceutical composition or coadministered as individual dosage units.

The following examples illustrate the invention without however implying a limitation.

In the following examples, the abbreviation "d" denotes density. The melting points (m.p.) are given in degrees Celsius; unless indicated otherwise, they were measured without recrystallization of the product. The purity of the products is checked by thin layer chromatography (TLC) or HPLC. The products are characterized by their NMR spectra run at 200 MHz in deuterated DMSO with tetramethylsilane as the internal reference. The specific optical rotations ([α]$_D$) are measured at 22° C.; path length, 10 cm; concentration, 1 g per 100 mL.

The following abbreviations are used in the interpretation of the NMR spectra:

s: singlet
t: triplet
q: quadruplet
quint: quintuplet
sext: sextuplet
m: unresolved signals or multiplet.

EXAMPLE 1

2-n-Butyl-4-spirocyclopentane-1-[(2'-(tetrazol-5-yl) biphenyl- 4-yl)methyl]-2-imidazolin-5-one A. 2-n-Butyl-4-spirocyclopentane-2-imidazolin-5-one The ethyl ester of 1-aminocyclopentanecarboxylic acid is prepared according to ADKINS and BILLICA (*J. Amer. Chem. Soc.*, 70, 3121 (1948)).

Ethyl valerimidate is prepared according to Mac ELVAIN (*J. Amer. Chem. Soc.*, 64, 1825–1827 (1942)) and then freed from its hydrochloride by reaction with potassium carbonate and extraction with DCM.

The ethyl ester of 1-aminocyclopentanecarboxylic acid (1.57 g) and ethyl valerimidate (1.56 g) are dissolved in 12 mL of xylene containing six drops of acetic acid. After refluxing for six and a half hours, the reaction medium is concentrated under vacuum and the residue is then chromatographed on silica gel using a chloroform/methanol/acetic acid mixture (94/4/2; v/v/v) as the eluent. The fraction containing the expected product is evaporated several times in the presence of xylene and then benzene in order to remove the acetic acid. 1.91 g of product are obtained in the form of a thick oil.

IR (CHCl$_3$): 1720 cm$^{-1}$; C=O. 1635 cm$^{-1}$: C=N. Note: The fact that there is no visible band between 1500 and 1600 cm$^{-1}$ indicates that, in chloroform solution, the product is an imidazolin-5-one.

| NMR spectrum |
| --- |
| 0.92 ppm:t:3 H:CH$_3$(nBu) |
| 1.35 ppm:sext:2 H:CH$_3$—CH$_2$— |
| 1.50–1.93 ppm:m:10 H:CH$_3$—CH$_2$—CH$_2$—and cyclopentane |
| 2.33 ppm:t:2 H:CH$_3$—CH$_2$—CH$_2$—CH$_2$— |
| 10.7 ppm:m:NH |

Mass spectrum: MH+: 195

The 2-n-butyl-4-spirocyclopentane-2-imidazolin-5-one prepared in step A can also be obtained by another procedure described below, using cyclopentanone as the starting material.

1. 1-Aminocyclopentanenitrile

This step is carried out according to A. Strecker (*Org. Synth.*, 3, (1933)).

Sodium cyanide (1.97 g) is dissolved in water (3.9 mL) in a round-bottomed flask and a solution containing 2.33 g of ammonium chloride in 5.9 mL of water and 3.5 mL of 20% aqueous ammonia is added; finally, 3 g of cyclopentanone in 3.8 mL of methanol are added to the flask. After stirring for one and a half hours, the mixture is heated at 60° C. for 45 minutes, heating is then stopped, stirring is continued for 45 minutes and the mixture is then cooled to 25° C. It is extracted several times with methylene chloride. The extracts are dried over sodium sulfate, filtered and concentrated under vacuum to give 4 g of the expected product in the form of an oil.

The 1-aminocyclopentanenitrile obtained is dissolved in 300 mL of acetone, and a solution of 2.25 g of oxalic acid dihydrate in 200 mL of acetone is added, with stirring. The precipitate formed is filtered off, washed with acetone and then dried.

m=4.71 g.
m.p.=220° C.

This compound is 1-aminocyclopentanenitrile hemioxalate.

2. 1-Aminocyclopentaneacetamide

This step is carried out according to J. Zabicky (*The Chemistry of Amides*, Interscience, New York, 119 (1970)).

5.1 g of the oxalate obtained in the previous step are treated with 7.65 mL of concentrated sulfuric acid (d=1.84) over 45 minutes, with stirring. The evolution of a gas is observed and the temperature rises to 100° C. The mixture is cooled to about 35° C. and poured into a mixture of ice and concentrated aqueous ammonia (10 g/2.8 mL). The suspension formed is extracted six times in succession with chloroform containing 5% of methanol. 3 mL of aqueous ammonia (d=0.92) are added to the aqueous phase and the mixture is extracted again with chloroform containing methanol (1/0.5; v/v). The combined organic phases are dried over sodium sulfate filtered and concentrated. The expected product is obtained in the form of a white solid.

m=3.79 g.
m.p.=95° C.

The structure can be confirmed by the results of analysis and the IR spectrum.

3. 2-n-Butyl-4-spirocyclopentane-2-imidazolin-5-one

This step is carried out according to H. Takenaka et al., *Heterocycles*, 29(6), 1185–89 (1989).

3 g of the compound prepared in the previous step are placed in 70 mL of anhydrous THF and 3.3 mL of triethylamine, and 3 mL of valeryl chloride in 10 mL of anhydrous THF are added, with stirring. A white suspension is formed. The intermediate which is formed, but not isolated, is 1-(N-valeryl)aminocyclopentanecarboxamide. 6 g of potassium hydroxide pellets, 7 mL of water and 16 mL of methanol are added. The mixture is refluxed for two and a half hours and 9 g of ammonium chloride are then added. After stirring for 15 minutes, the mixture is concentrated under vacuum. The residue obtained is taken up in 40 mL of water and extracted with 10 mL of ethyl acetate and then twice with 5 mL of ethyl acetate. The combined organic phases are dried over sodium sulfate and filtered. The filtrate is concentrated to dryness to give 4.85 g of the expected product. The NMR spectrum is similar to that described previously. The hydrochloride of this compound can be prepared by the addition of concentrated hydrochloric add. The hydrochloride melts at 240° C. with sublimation.

B. 1-[(2'-Cyanobiphenyl-4-yl)methyl]-2-n-butyl-4 -spirocyclopentane-2-imidazoliin-5-one A mixture containing 250 mg of sodium hydride (as an 80% dispersion in mineral oil) and 5 mL of DMF is prepared under a nitrogen atmosphere and a solution containing 0.97 g of 2-n-butyl-4-spirocyclopentane-2-imidazolin-5-one (prepared in step A) in 10 mL of DMF is added dropwise. The mixture is stirred for 30 minutes at room temperature and a solution of 1.5 g of 4-bromomethyl-2'-cyanobiphenyl in 10 mL of DMF is then added. After stirring for one hour at room temperature, the DMF is evaporated off under reduced pressure, the residue is then taken up with ethyl acetate and the organic phase is washed with water and then dried over sodium sulfate, filtered and evaporated. The residue is chromatographed on silica gel using a DCM/ethyl acetate mixture (9/1; v/v) as the eluent. 1.68 g of the expected product are recovered. m.p.=92°–93° C.

C. 2-n-Butyl-4-spirocyclopentane-1-[(2'-(triphenylmethyltetrazole- 5-yl)biphenyl-4-yl)methyl]-2-imidazolin-5-one 1.56 g of the previous product, 2.6 g of tributyltin azide and 30 mL of xylene are refluxed for 66 hours. The xylene is then evaporated off and the residue is dissolved in 20 mL of DCM and 5 mL of THF with the addition of 0.8 mL of 10N sodium hydroxide solution and, after stirring for 30 minutes, 2.5 g of trityl chloride and the mixture is stirred for 26 hours. After evaporation of the solvents, the residue is taken up in ethyl acetate, washed with water and then with a 3% solution of potassium bisulfate and water. It is dried and evaporated. The residue is chromatographed on alumina using a hexane/ethyl acetate mixture (9/1; v/v) as the eluent to give 1.97 g of the expected product. m.p.=150°–152° C.

D. 2-n-Butyl-4-spirocyclopentane-1-[(2'-(tetrazol-5-yl)biphenyl- 4-yl)methyl]-2-1midazolin-5-one 1.96 g of the product prepared in the previous step are dissolved in 10 mL of methanol and 10 mL of THF. After the reaction medium has been cooled to 5° C., 1.5 mL of 4N hydrochloric acid are added and the mixture is stirred for three hours at room temperature and one hour at 30° C. After evaporation of the solvents, the residue is taken up in water and the pH is brought to 12 by the addition of 10N sodium hydroxide solution. The aqueous phase is extracted with ether, toluene and ether again. The aqueous phase is acidified to pH 2 by the addition of 1N hydrochloric acid and then extracted with ethyl acetate and the extract is dried and evaporated. The white solid obtained is dried at 50° C. under 0.05 mm of mercury to give 840 mg of the expected product. m.p.=180°–181° C.

| -NMR spectrum |
| --- |
| 0.75 ppm:t:3 H;CH$_3$(nBu) |
| 1.10 ppm:sext:2 H:CH$_3$—CH$_2$— |
| 1.20 ppm:quint:2 H:CH$_3$—CH$_2$—CH$_2$— |
| 1.5–2 ppm:m:8 H:—C$_5$H$_8$— |
| 2.2 ppm:t:2 H:CH$_3$—CH$_2$—CH$_2$—CH$_2$— |
| 4.6 ppm:s:2 H:C$\underline{H}_2$—C$_6$H$_4$—. |
| 7 ppm:s:4 H:CH$_2$—C$_6$H$_4$— |
| 7.35–7:7 ppm:m:4 H:aromatic H$_{3',4',5',6'}$ |

An NOE study confirms the position of the 5-one substituent on the imidazole.

EXAMPLE 2

Potassium salt of 2-n-Butyl-4-spirocyclopentane-1-[(2'-(tetrazol-5-yl) biphenyl-4-yl)methyl]-2-imidazolin-5-one 970 mg of the compound obtained in Example 1 are dissolved in 40 mL of an isopropanol/methanol mixture (1/1; v/v) and the pH is adjusted to 12 by the addition of an 85% solution of potassium hydroxide in a methanol/water mixture (20/1; v/v). The reaction medium is evaporated, the residue is taken up in isopropanol and the medium is evaporated again. The residue is dissolved in 20 mL of isopropanol, with gentle heating, and then left to return to room temperature. The mixture is left to decant, the filtrate is evaporated and the residue is then taken up in heptane. After trituration, the product solidifies; it is filtered off and then washed again with heptane and dried under vacuum to give 945 mg of the expected potassium salt.

m.p.=142°–144° C.

Elemental analysis: C$_{25}$H$_{27}$KN$_6$O.H$_2$O. calc. % C, 61.95; H, 6.03; N, 17.23. Found % 62.02; 6.13; 17.14.

What is claimed is:

1. A method for treating cardiac arrhythmia which comprises administering to a patient in need thereof a therapeutically effective amount of a compound having the structure

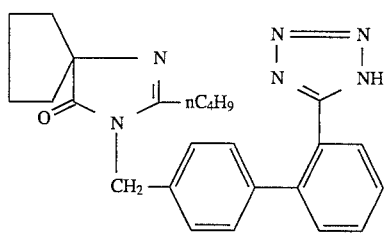

or a pharmaceutically acceptable salt thereof.

2. The method of claim 1 wherein the pharmaceutically acceptable salt of the compound having the structure I is a sodium salt.

3. The method of claim 1 wherein the pharmaceutically acceptable salt of the compound having the structure I is a potassium salt.

4. The method of claim 1 wherein the compound having the structure I or a pharmaceutically acceptable salt thereof is administered in an amount of from about 0.5 to about 5000 mg per day.

5. The method of claim 1 wherein the compound having the structure I or a pharmaceutically acceptable salt thereof is administered in an amount of from about 1 to 2500 mg per day.

6. The method of claim 1 wherein the compound having the structure I or a pharmaceutically acceptable salt thereof is administered as a single daily dose.

7. The method of claim 1 wherein the compound having the structure I or a pharmaceutically acceptable salt thereof is in association with a beta-blocking compound.

8. The method of claim 1 wherein the compound having the structure I or a pharmaceutically acceptable salt thereof is in association with a diuretic compound.

9. The method of claim 1 wherein the compound having the structure I or a pharmaceutically acceptable salt thereof is in association with a non-steroidal antiinflammatory compound.

10. The method of claim 1 wherein the compound having the structure I or a pharmaceutically acceptable salt thereof is in association with a calcium antagonist compound.

11. The method of claim 1 wherein the compound having the structure I or a pharmaceutically acceptable salt thereof is in association with a tranquilizer compound.

12. The method of claim 1 wherein the compound having the structure I or a pharmaceutically acceptable salt thereof is in association with another antiarrhythmic agent.

* * * * *